(12) United States Patent  (10) Patent No.: US 7,341,583 B2
Shiono et al.  (45) Date of Patent: Mar. 11, 2008

(54) POSITIONING SYSTEM FOR AN APPLICATOR AND POSITIONING METHOD FOR AN APPLICATOR

(75) Inventors: Hiroshi Shiono, Tokyo (JP); Akira Sakaguchi, Minami-Ashigara (JP); Shin Maki, Somerset, NJ (US)

(73) Assignee: Terumo Kabushiki Kaisha, Tokyo (JP)

( * ) Notice: Subject to any disclaimer, the term of this patent is extended or adjusted under 35 U.S.C. 154(b) by 747 days.

(21) Appl. No.: 10/809,543

(22) Filed: Mar. 26, 2004

(65) Prior Publication Data

US 2004/0249269 A1  Dec. 9, 2004

(30) Foreign Application Priority Data

Mar. 27, 2003 (JP) ............... 2003-087932

(51) Int. Cl.
*A61B 18/18* (2006.01)
(52) U.S. Cl. .............. 606/13; 606/23; 606/27; 607/116; 607/138; 607/143; 600/424; 600/448
(58) Field of Classification Search ........... 606/13–16, 606/27, 28; 607/116, 138, 143; 128/898; 600/424, 437, 443–493; 73/596, 627–632
See application file for complete search history.

(56) References Cited

U.S. PATENT DOCUMENTS

| 4,791,926 | A | * | 12/1988 | Fry ................. 606/7 |
| 5,234,004 | A | | 8/1993 | Hascoet et al. |
| 5,620,480 | A | * | 4/1997 | Rudie ................. 607/101 |
| 5,623,940 | A | * | 4/1997 | Daikuzono ............ 600/439 |
| 6,004,269 | A | * | 12/1999 | Crowley et al. ......... 600/439 |
| 6,106,517 | A | * | 8/2000 | Zupkas ................. 606/20 |
| 6,361,531 | B1 | * | 3/2002 | Hissong ............... 606/27 |
| 6,383,183 | B1 | | 5/2002 | Sekino et al. |
| 6,589,171 | B2 | * | 7/2003 | Keirsbilck ............ 600/300 |
| 6,605,082 | B2 | * | 8/2003 | Hareyama et al. ....... 606/11 |
| 6,788,967 | B2 | * | 9/2004 | Ben-Haim et al. ....... 600/424 |

FOREIGN PATENT DOCUMENTS

JP  11-318928  11/1999
JP  2000-271235  10/2000

* cited by examiner

*Primary Examiner*—A. Farah
(74) *Attorney, Agent, or Firm*—Buchanan Ingersoll & Rooney, PC (57) ABSTRACT

A positioning system for an applicator includes a glove for being used for a diagnosis of the affected part, a mark body provided on the glove, an applicator for being inserted into a living body, and an energy emitter provided on the applicator for supplying energy to the living body. The positioning system further includes a sensor provided on the applicator which is capable of detecting the distance to the mark body, a control apparatus for discriminating an optimum position of the applicator based on the distance between the sensor and the mark body while the mark body is disposed in the proximity of the affected part based on a diagnosis performed using the glove, and a display apparatus for displaying a result of the discrimination by the control apparatus.

21 Claims, 8 Drawing Sheets

POSITIONING SYSTEM FOR AN APPLICATOR AND POSITIONING METHOD FOR AN APPLICATOR

BACKGROUND OF THE INVENTION

1. Field of the Invention

This invention relates to a positioning system and a positioning method for an applicator which can present an optimum position of an applicator inserted in a living body to an operator in order to treat an affected part of the patient.

2. Description of the Prior Art

As one of treating methods for a disease in a living body such as a tumor or a hypertrophy, a method is known wherein energy is applied to the affected part to cause coagulation or sphacelation of the cells at the affected part. One of measures for applying energy is an applicator for heating the affected part, for example, by laser heating.

In the treatment, if some other sound part of the living body than the affected part is laser heated, then even the sound part is damaged. On the other hand, if the affected part is not laser heated appropriately, then a sufficient treatment effect may not be achieved. Accordingly, the positioning of the applicator is very significant in the treatment and must be conducted carefully.

Various techniques have conventionally been proposed for the positioning of an applicator.

Prior Art (1)

A technique is available wherein a probe having an ultrasonic transmission/reception section provided thereon together with an applicator is inserted into a body cavity. The probe can form an intracorporeal sectional image by transmitting and receiving an ultrasonic wave in the body cavity. Accordingly, a user such as a doctor can position the applicator while observing the intracorporeal sectional image (refer to, for example, Japanese Patent Laid-Open No. 2000-271235).

Prior Art (2)

Another technique is available wherein a probe having an endoscope built therein together with an applicator is inserted into a body cavity. A user can position the applicator while observing the internal surface of a living body by means of the endoscope via an opening provided in the probe (refer to Japanese Patent Laid-Open No. Hei 11-318928 or U.S. Pat. No. 6,383,183).

SUMMARY OF THE INVENTION

It is an object of the present invention to provide a positioning system and a positioning method for an applicator which can simplify a treatment system without the necessity for an image production apparatus, can reduce the burden on the patient and can make it possible to position the applicator readily at an optimum position.

(1) According to an aspect of the present invention, there is provided a positioning system for an applicator, comprising a diagnosing implement to diagnose of a living body including an affected part, a mark body provided on said diagnosing implement, an applicator, an energy emitter provided in said applicator and emitting energy to the living body, at least one sensor provided on said applicator for outputting a signal corresponding to a distance between the sensor and said mark body, and an indicator which indicate a preferable position of said applicator based on the output of said sensor while said mark body is disposed in the proximity of the affected part through a diagnosis performed using said diagnosing implement.

With the positioning system for an applicator, since the mark body is provided on the diagnosing implement, while a doctor or the like diagnoses the affected part of a patient using the diagnosing implement, it can dispose the mark body using the same as a mark representative of the position of the affected part. Since the distance to the mark body can be detected by means of the sensor, the optimum position of the applicator can be discriminated based on the detected distance. Since the information detected by the sensor is presented by means of the presentation means, the user can position the applicator readily at the affected part in accordance with the presentation.

(2) According to another aspect of the present invention, there is provided a positioning system for an applicator, comprising an applicator, an energy emitter provided in said applicator and emitting energy to a living body, a mark body provided on said applicator, a diagnosing implement to diagnose of a living body including an affected part, a sensor provided on said diagnosing implement and capable of detecting a distance between the sensor and said mark body, and an indicator which indicates a preferable position of said applicator based on an output of said sensor while said sensor is disposed in the proximity of the affected part through the diagnosis performed using said diagnosing implement.

With the positioning system for an applicator, since the sensor is provided on the diagnosing implement, while a doctor or the like diagnoses the affected part of a patient using the diagnosing implement, it can dispose the sensor at the position of the affected part. Since the sensor can detect the distance to the mark body provided on the applicator, the optimum position of the applicator can be discriminated based on the detected distance. Since the information detected by the sensor is presented by means of the presentation means, the user can position the applicator readily at the affected part in accordance with the presentation.

(3) According to a further aspect of the present invention, there is provided a positioning method for an applicator, comprising the steps of diagnosing a living body including an affected part with a diagnosing implement which has a mark body, specifying the position of the affected part and disposing the mark body in the proximity of the affected part, inserting an applicator having a sensor capable of detecting the distance between the sensor and said mark body into the living body, and positioning said applicator in response to information indicated corresponding to an output of said sensor.

With the positioning method for an applicator, since the mark body is provided on the diagnosing implement, while a doctor or the like diagnoses the affected part of a patient using the diagnosing implement, it can dispose the mark body using the same as a mark representative of the position of the affected part. Since the distance to the mark body can be detected by means of the sensor, the optimum position of the applicator can be discriminated based on the detected distance. Since the information detected by the sensor is presented by means of presentation means, the user can position the applicator readily at the affected part in accordance with the presentation.

(4) According to a still further aspect of the present invention, there is provided a positioning method for an applicator, comprising the steps of diagnosing a living body including an affected part with a diagnosing implement which has a sensor specifying the position of the affected part and disposing the sensor in the proximity of the affected part, inserting an applicator having a mark body into a living body, detecting the distance between of said sensor and the mark body, and positioning said applicator in response to information detected by said sensor.

With the positioning system for an applicator, since the sensor is provided on the diagnosing implement, while a doctor or the like diagnoses the affected part of a patient using the diagnosing implement, it can dispose the sensor at the position of the affected part. Since the sensor can detect the distance to the mark body provided on the applicator, the optimum position of the applicator can be discriminated based on the detected distance. Since the information detected by the sensor is presented by means of presentation means, the user can position the applicator readily at the affected part in accordance with the presentation.

The above and other objects, features and advantages of the present invention will become apparent from the following description and the appended claims, taken in conjunction with the accompanying drawings in which like parts or elements denoted by like reference symbols.

DETAILED DESCRIPTION OF THE INVENTION

Preferred embodiments of the present invention will now be described in detail with reference to the drawings.

Figure 1:
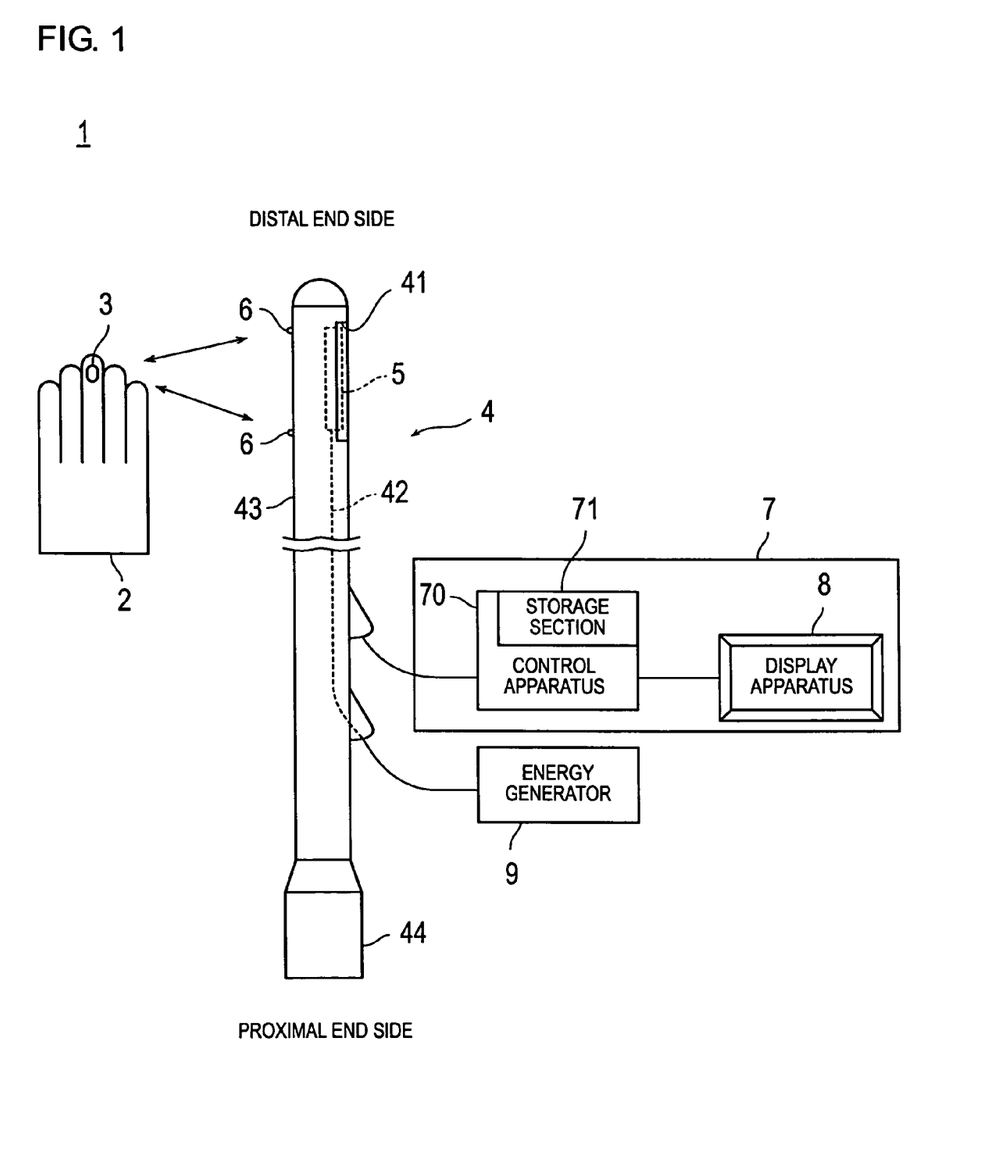
FIG. 1 is a schematic view showing a configuration of a positioning system for an applicator.

FIG. 1 is a schematic view showing a positioning system for an applicator. It is to be noted that various components shown in FIG. 1 are represented individually in a simplified shape and in a suitable size so as to facilitate understanding of the applicator positioning system.

Referring to FIG. 1, the positioning system 1 for an applicator (hereinafter referred to simply as system 1) includes a glove 2 (diagnosing implement) for being used for a diagnosis of an affected part of a patient, a mark body 3 provided on the glove 2, an applicator 4 for being inserted into a living body to treat the living body, and an energy emitter 5 provided on the applicator 4 for emitting energy to the living body. The system 1 further includes two sensors 6 provided on the applicator 4 in a substantially neighboring relationship to the energy emitter 5 for detecting the distance to the mark body 3, a control apparatus 70 (processor) for discriminating an optimum position of the applicator 4 based on the distance between the sensor 6 and the mark body 3 while the mark body 3 is disposed in the proximity of the affected part based on a diagnosis performed using the glove 2, and a display apparatus 8 for displaying a result of the discrimination by the control apparatus 70. The control apparatus 70 and the display apparatus 8 may be referred to generally as indicator 7.

The glove 2 is formed so thin that it may not degrade a delicate feeling of a finger and formed so tough that it may not be broken during treatment. For example, natural rubber latex is used as the material for the glove 2. The glove 2 is in a sterilized state in order to prevent an otherwise possible infectious disease.

Also the mark body 3 is in a sterilized state similarly. The mark body 3 may be in any form only if it can be detected by the sensor 6. For example, where the sensor 6 is an elastic wave sensor preferably an ultrasonic wave sensor 6, the mark body 3 is formed from an ultrasonic wave reflecting element such as a metal piece. The ultrasonic wave reflecting member is a body having an acoustic impedance different from that of a living body and may otherwise be the air or the like other than a metal piece. Where the air is used as the mark body 3, the air is filled in and attached together with a balloon to the glove 2.

The attached position of the mark body 3 preferably corresponds to the tip of a finger of the glove 2. Where the mark body 3 is provided at the top of a finger, while the user keeps a posture in which it has confirmed the affected part through palpation, it can dispose the mark body 3 substantially at the middle of the affected part. The mark body 3 is formed small in size and in thickness so that it may not degrade the feeling of a finger of the user upon palpation. The mark body 3 is preferably formed in a substantially disk-like shape free from any angle.

The applicator 4 has an insertion portion 43 formed long in a tapering fashion toward the distal end thereof and has a holding portion 44 provided on a proximal end side thereof and having a shape with which the holding portion 44 can be held readily. The insertion portion 43 has the energy emitter 5 built therein and has a window 41 provided therein for radiating energy toward the living body therethrough. The energy emitter 5 is connected to an energy generator 9 through an energy route 42 extending along the inside of the insertion portion 43. The energy generator 9 generates energy in accordance with an instruction by the user to start a diagnosis. Here, the energy generated by the energy generator 9 is an electromagnetic wave such as a laser beam, a microwave or a radio frequency wave and is supplied from the energy emitter 5 to the affected part to heat and treat the affected part.

Two sensors 6 are provided in the proximity of the energy emitter 5. The sensors 6 are disposed at positions spaced equally from the center of the energy emitter 5 and the window 41 in a juxtaposed relationship on a straight line parallel to the lengthwise direction of the insertion portion 43. The sensors 6 are preferably provided on an outer face of the insertion portion 43 in order to detect the mark body 3 provided on the glove 2. The sensors 6 are connected to the control apparatus 70 through signal lines not shown which extend through the inside of the insertion portion 43. Also the display apparatus 8 is connected to the control apparatus 70. The control apparatus 70 includes a storage section 71 for storing predetermined information.

Figure 2:
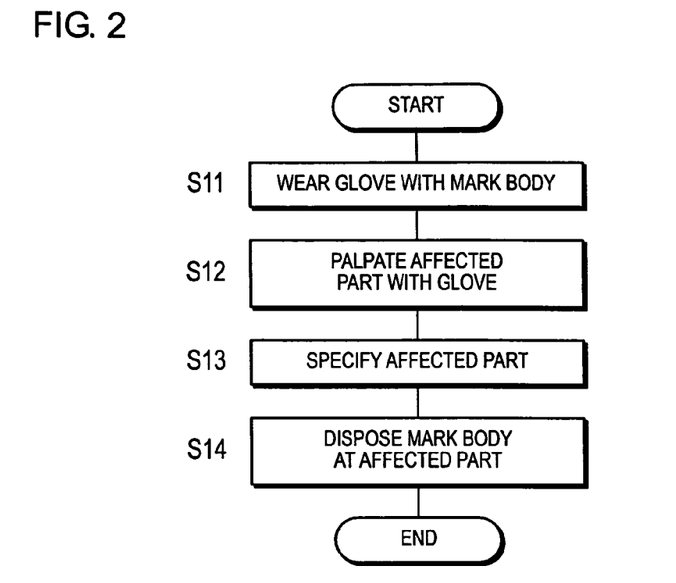
FIG. 2 is a flow chart illustrating a flow of operation of the user when it specifies an affected part of a patient.
Figure 3:
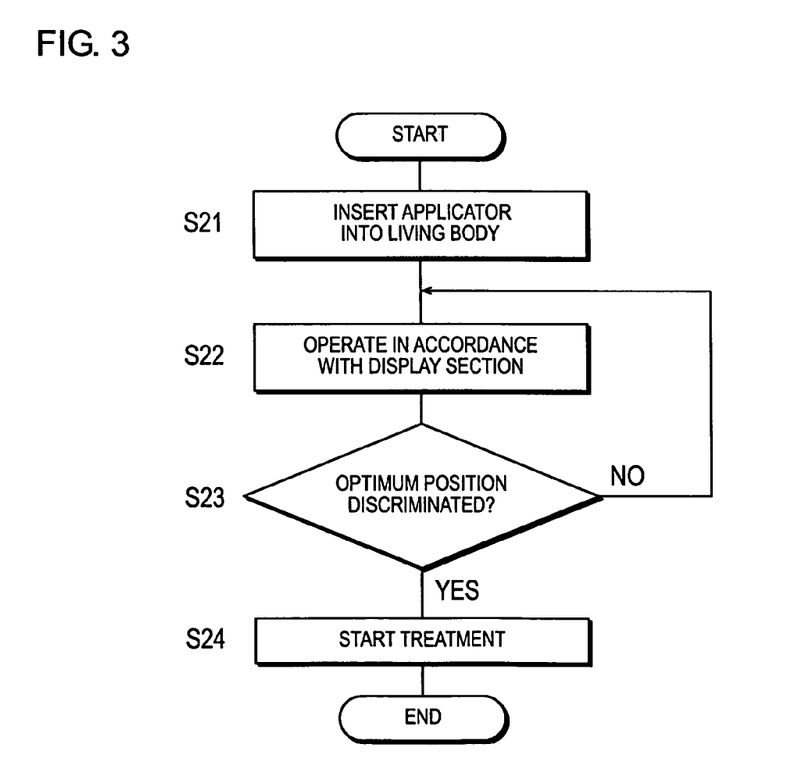
FIG. 3 is a flow chart illustrating a flow of operation of the user when it confirms an optimum position of the applicator.
Figure 4:
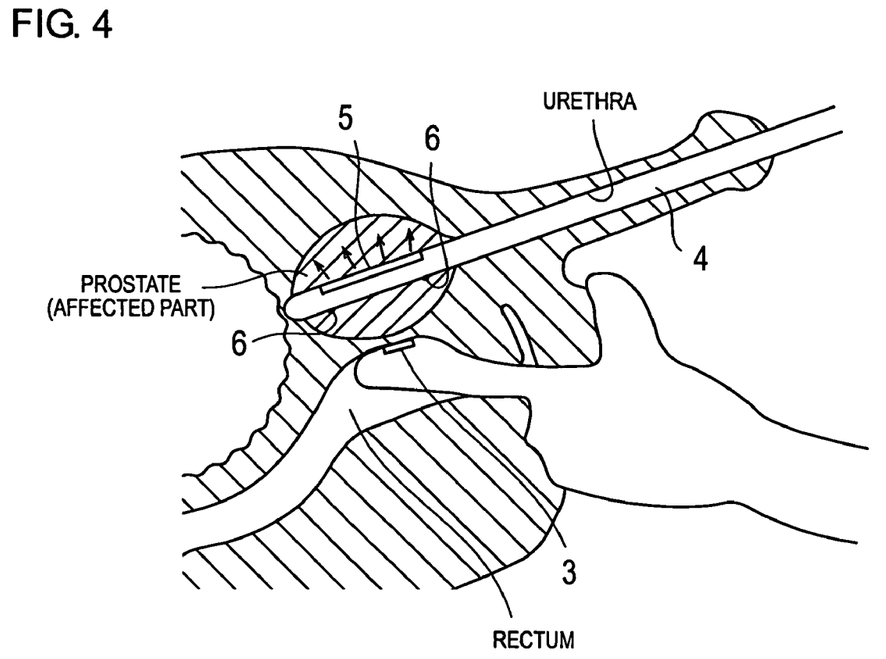
FIG. 4 is a schematic view illustrating a manner in which the user treats the affected part.

Now, description is given of how the system 1 is used for treatment by the user with reference to FIGS. 2 to 4. The following description relates to a case wherein treatment of prostatic hypertrophy is conducted.

FIG. 2 is a flow chart illustrating a flow of operation of the user when it specifies an affected part of a patient; FIG. 3 is a flow chart illustrating a flow of operation of the user when it confirms the optimum position of the applicator 4; and FIG. 4 is a schematic view illustrating a manner in which the user treats the affected part.

First, the user would wear the glove 2 on which the mark body 3 is provided in preparation for the treatment (step S11). Then, the user would fill the rectum with physiological saline or sterilized water, insert the finger on which the mark body 3 is provided (for example, the middle finger) into the rectum and start the palpation of the affected part (step S12). Here, in the case of the prostatic hypertrophy, the most swollen portion of the spherical prostate is the center of the affected part.

The user would specify the most swollen portion of the prostate as the affected part through the palpation (step S13) and dispose the mark body 3 at the position of the specified affected part (step S14). Here, the user would closely contact the mark body 3 with the wall of the rectum on the affected part side. This is intended to facilitate propagation of the ultrasonic wave. Since the palpation of the user is used, the most swollen portion of the prostate can be specified readily.

While the user keeps the state wherein it inserts the middle finger in the rectum and disposes the mark body 3 at the affected part, it would insert the insertion portion 43 of the applicator 4 into the living body (step S21). Here, since the treatment of the prostatic hypertrophy is to be performed, the applicator 4 is inserted into the urethra.

The user would operate the applicator 4 in accordance with a display of the display apparatus 8 to position the applicator 4 (step S22). The user would discriminate whether or not a display of an optimum position is given on the display apparatus 8 (step S23). If a display of an optimum position is not given (step S23: NO), then the positioning is continued. If a display of an optimum position is given (step S23: YES), then the user would fix the applicator 4 at the position and start treatment of the affected part (step S24). Here, to start treatment particularly signifies to turn the switch of the energy generator 9 ON to instruct the system 1 to supply the energy. The prostate surrounds the urethra as seen in FIG. 4. In order to treat the prostatic hypertrophy part, the applicator 4 is rotated successively by an arbitrary angle to supply the energy to the prostatic hypertrophy part.

Now, action of the system 1 is described with reference to FIGS. 5 to 9.

Figure 5:
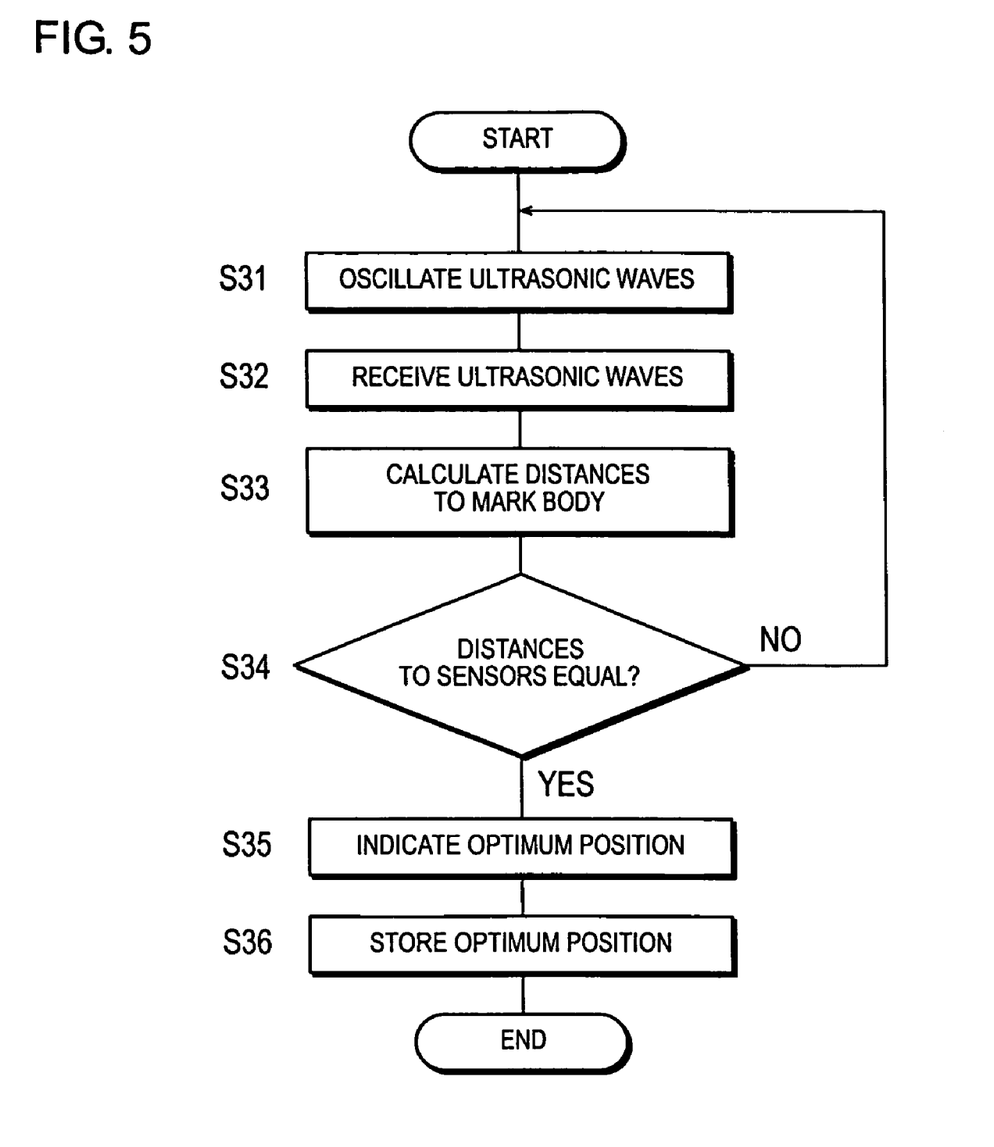
FIG. 5 is a flow chart illustrating a flow of operation when the system discriminates the optimum position of the applicator.
Figure 6:
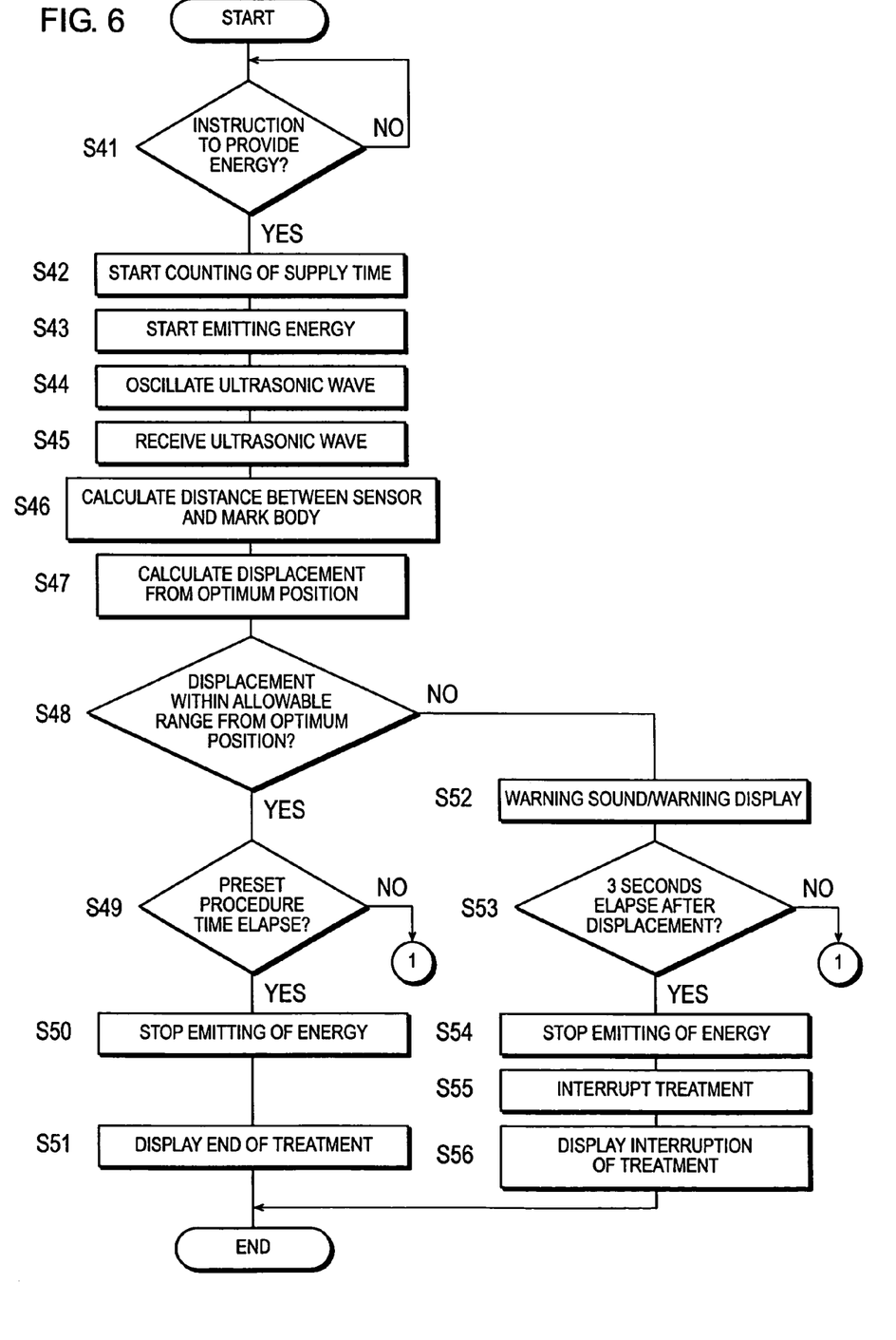
FIG. 6 is a flow chart illustrating a flow of operation when the system detects a positional displacement.
Figure 7:
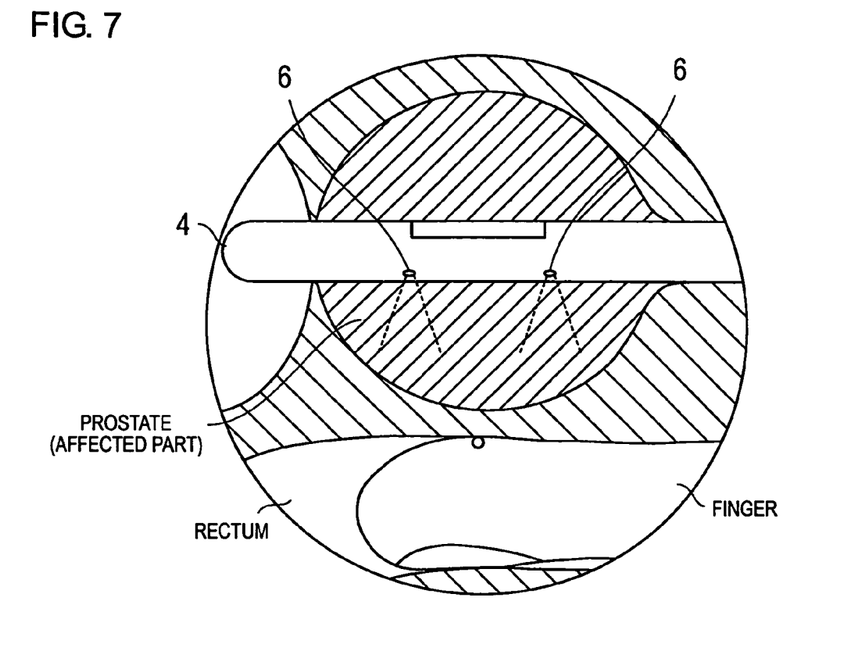
FIG. 7 is a view illustrating a manner wherein a mark body is detected by two sensors.
Figure 8:
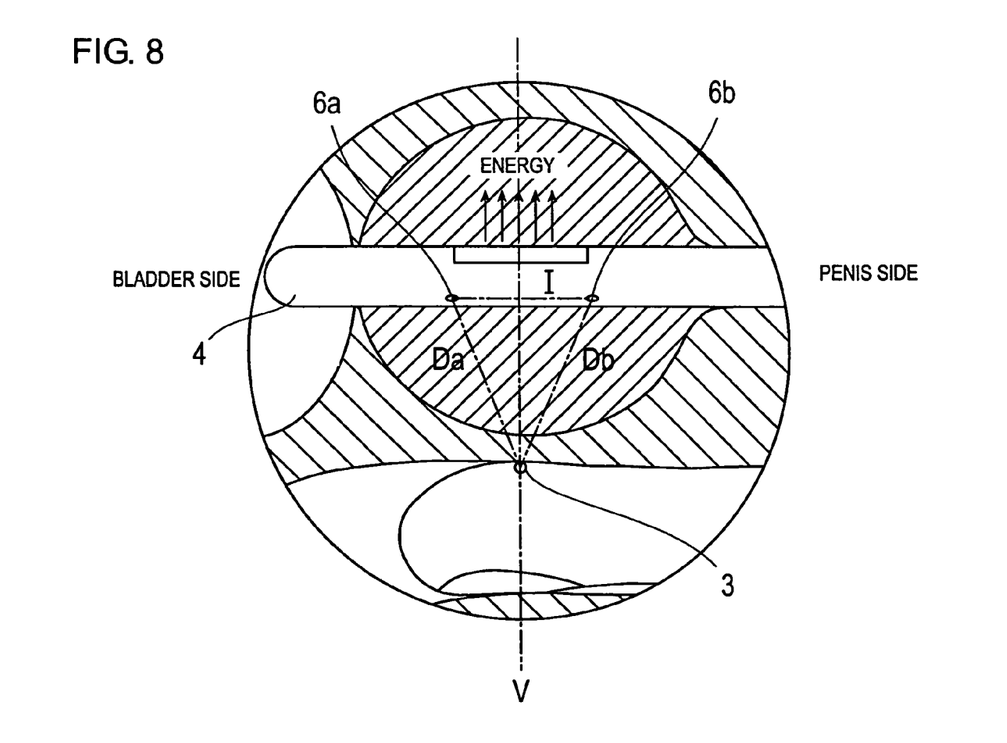
FIG. 8 is a similar view but illustrating a manner wherein it is discriminated whether or not the applicator is at the optimum position.
Figure 9:
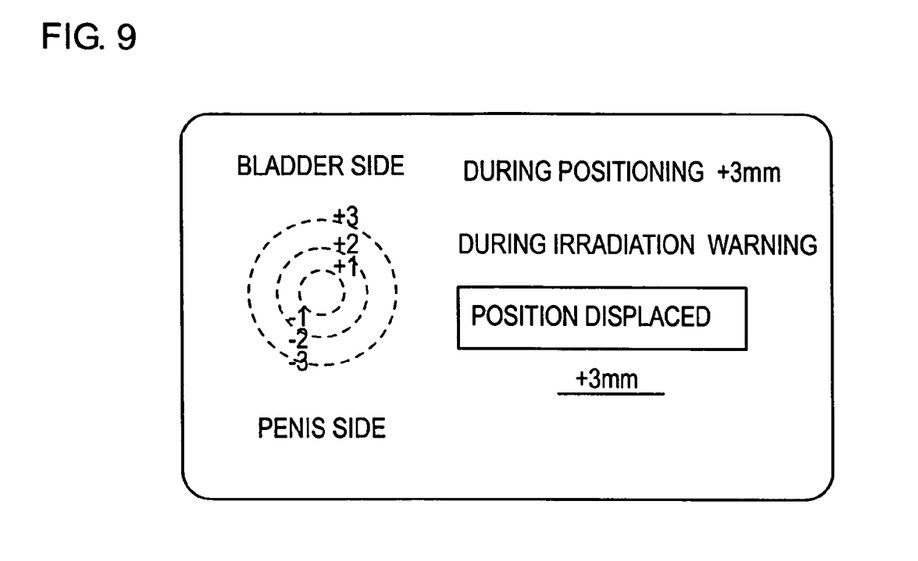
FIG. 9 is a view showing a screen displayed on a display apparatus.

FIG. 5 is a flow chart illustrating a flow of operation when the system 1 discriminates the optimum position of the applicator; FIG. 6 is a flow chart illustrating a flow of operation when the system 1 detects a positional displacement; FIG. 7 is a view illustrating a manner wherein the mark body 3 is detected by two sensors 6; FIG. 8 is a similar view but illustrating a manner wherein it is discriminated whether or not the applicator is at the optimum position; and FIG. 9 is a view showing a screen displayed on the display apparatus 8. The procedure illustrated in FIG. 5 indicates operation after the processes at steps S11 to S21 illustrated in FIGS. 2 and 3 are completed. Further, in the following description, the sensor 6 is an ultrasonic wave sensor 6, and the mark body 3 is a metal piece.

The system 1 starts oscillation of an ultrasonic wave having directivity by means of the sensors 6 as seen in FIG. 7 (step S31). If the mark body 3 is present at a position at which the ultrasonic wave hits on the same, then since the ultrasonic wave is reflected by the mark body 3, the sensors 6 receive the reflected ultrasonic wave and output reception signals to the control apparatus 70 (step S32). The control apparatus 70 measures the periods of time required to receive the ultrasonic wave after oscillated and calculates the distances to the mark body 3 based on the measured periods of time (step S33).

The control apparatus 70 discriminates whether or not the distances to the mark body 3 calculated with regard to the two sensors 6 are substantially equal to each other (step S34). If they are not equal to each other (step S34: NO), then the processes at the steps beginning with step S31 are repeated. If the distances (Da, Db) are substantially equal to each other (step S34: YES) as seen in FIG. 8, then the control apparatus 70 discriminates that the applicator 4 is now at its optimum position and controls the display apparatus 8 to display that the applicator 4 is at the optimum position (step S35). The control apparatus 70 stores the distances between the sensors 6 and the mark body 3 when it is discriminated that the applicator 4 is at its optimum position into the built-in storage section 71 (step S36). Then, the processing advances to the procedure illustrated in FIG. 6.

The control apparatus 70 discriminates whether or not an energy supplying instruction is inputted by the user (step S41). The control apparatus 70 waits until an energy supplying instruction is inputted (step S41: NO). If such an instruction is inputted (step S41: YES), then the control apparatus 70 starts counting of the period of time for the energy supply (step S42). Simultaneously, the energy emitter 5 starts supply of energy to the affected part (step S43).

Further, the system 1 periodically oscillates ultrasonic waves by means of the two sensors 6 (step S44) and receives the ultrasonic waves reflected by and returned from the mark body 3 (step S45). The control apparatus 70 measures the periods of time before the reception after the oscillation of the ultrasonic wave is started and then calculates the distances to the mark body 3 (step S46). Further, the control apparatus 70 calculates, based on the calculated distances, a positional displacement from the position then to the optimum position of the applicator 4 stored in the storage section 71 (step S47).

The control apparatus 70 discriminates whether or not the positional displacement is within an allowable range (step S48). If the positional displacement is within the allowable range (step S48: YES), then the control apparatus 70 refers to the count value of the period of time of the energy supply started at step S42 to discriminate whether or not a period of time for supply set as a period of time necessary for the intended treatment elapses (step S49). If the preset time period does not elapse (step S49: NO), then the processing returns to step S44 while the control apparatus 70 continues the supply of energy. However, if the preset time period elapses based on the count value of the supply time period (step S49: YES), then the control apparatus 70 stops the energy supply (step S50) and controls the display apparatus 8 to display that the treatment is completed (step S51), thereby ending the treatment process for the affected part.

On the other hand, if the positional displacement of the applicator 4 from the optimum position is outside the allowable range (step S48: NO), then the display apparatus 8 issues alarming sound and displays a warning display on the screen thereof as seen in FIG. 9 (step S52). In response to the warning, the user can correct the positional displacement. The control apparatus 70 discriminates whether or not 3 seconds or more elapse after the positional displacement occurs (step S53). Thus, the control apparatus 70 repeats the detection of the positional displacement at steps S44 to 48 for the period of time of 3 seconds (step S53: NO). If the positional displacement is corrected within the period, then the processing advances from step S48 to step S49.

However, if 3 seconds or more elapse after the occurrence of the positional displacement (step S53: YES)), then the energy emitter 5 interrupts the supply of energy (step S54) and the treatment is interrupted (step S55). Here, it is assumed that the period of time after the positional displacement occurs is measured after the control apparatus 70 discriminates at step S48 that the positional displacement is outside the allowable range. Then, the display apparatus 8 displays that the treatment is interrupted (step S56) to notify the user of the interruption and then waits until the applicator 4 is returned to the appropriate position and the treatment is resumed.

Now, the foundation on which it is discriminated at step S34 that the applicator 4 is at its optimum position when the distances to the mark body 3 detected by the two sensors 6 are equal to each other is described with reference to FIG. 8.

In FIG. 8, an imaginary chain line V is indicated at a position at which the mark body 3 is disposed. As described hereinabove, the two sensors 6 are disposed at distances equal to each other from the center of the energy emitter 5. In other words, the center of the energy emitter 5 is positioned at the center between the two sensors 6.

The sensor 6 on the left side in FIG. 8 is represented as sensor 6a while the sensor 6 on the right side is represented as sensor 6b. The distances to the mark body 3 calculated based on transmission and reception of ultrasonic waves by the sensors 6a and 6b are represented as distance Da and distance Db, respectively. Further, a point at which a straight line interconnecting the sensors 6a and 6b and the imaginary chain line V intersect with each other is represented as intersecting point I.

When the distance Da and the distance Db are not equal to each other, the triangle including the three points of the sensor 6a, sensor 6b and mark body 3 do not make an isosceles triangle. Accordingly, since the distance from the sensor 6a to the intersecting point I and the distance from the sensor 6b to the intersecting point I are not equal to each other, the center of the energy emitter 5 and the mark body 3 are displaced in position from each other.

On the other hand, where the distance Da and the distance Db are equal to each other, the triangle including the three points of the sensor 6a, sensor 6b and mark body 3 is an isosceles triangle. Accordingly, since the distance from the sensor 6a to the intersecting point I and the distance from the sensor 6b to the intersecting point I are equal to each other, the center of the energy emitter 5 and the mark body 3 coincide in position with each other. In other words, the positions of the center of the energy emitter 5 and the center of the affected part coincide with each other. In this instance, the energy emitter 5 can irradiate energy radially from the center of the affected part. Consequently, energy can be supplied sufficiently to the affected part.

From the reason described, it can be determined that the applicator 4 is at its optimum position where the distance Da and the distance Db are equal to each other.

It is to be noted that the allowable range for the discrimination of the positional displacement at step S48 is determined in advance from the point of view of whether or not the supply of energy in the state of the positional displacement has a seriously bad influence on the living body.

As described above, according to the system 1 of the present embodiment, since the mark body 3 is provided on the glove 2, the user can dispose the mark body 3 as a mark indicative of the position of the affected part while the user performs palpation using the glove 2. Since the distances to the mark body 3 can be detected by means of the sensors 6, the optimum position of the applicator 4 can be discriminated based on the detected distances. Since a result of the discrimination is displayed by the display apparatus 8, the user can position the applicator 4 at the affected part readily in accordance with the display.

Further, since the sensor 6 oscillates an ultrasonic wave and besides receives it, the configuration of the applicator 4 is simplified and the diameter of the applicator 4 can be reduced. Consequently, the burden on the patient can be reduced. Furthermore, since the mark body 3 has an acoustic impedance different from that of a living body, it is detected with certainty by means of the sensors 6.

Further, since the two sensors 6 are provided, if the distances from the sensors 6 to the mark body 3 are calculated, then when the distances coincide with each other, the position of the applicator 4 then can be discriminated decisively as the optimum position.

Since the display apparatus 8 displays it by sound and an image that the applicator 4 is positioned at its optimum position, the user can confirm the optimum position of the applicator 4 using the auditory sense and the visual sense thereof, respectively. It is to be noted that the presentation to the user may be based on either one of an image and sound.

Further, since the display apparatus 8 displays a warning by sound and an image also when the position of the applicator 4 is displaced from the optimum position, the user can confirm the warning using the auditory sense and the visual sense thereof, respectively. Although a technique that an expansion portion which can be expanded by an extracorporeal operation is provided and hooked intracorporeally in order to fix the position of the applicator 4 is conventionally available, a defect of the technique can be overcome. In particular, since a patient has some individual difference, the applicator 4 cannot necessarily be fixed by the expansion portion of the conventional technique, and even if some positional displacement occurs with the applicator 4, this cannot be detected and there is the possibility that the normal living body may be damaged. However, according to the present embodiment, although the applicator 4 is not fixed by a special mechanism, since a positional displacement can be detected, a sufficient treatment effect can be achieved without damaging the normal living body. It is to be noted that the presentation of the warning may be performed by one of an image and sound.

Further, since the mark body 3 can be sterilized, it does not give rise to an infectious disease and can be introduced into the living body in safety. Since the mark body 3 is thin and small and is formed in a substantially round shape free from an angle so that it may not have an influence on the palpation, the user can perform the palpation without degradation of the delicate feeling of the fingertip.

Furthermore, the embodiment described above is suitable for treatment of the prostatic hypertrophy because the applicator 4 is inserted in the urethra and the sensor 6 is disposed in the rectum.

(Modifications, Etc.)

Now, particular operations or different operations of and modifications to the components described above in connection with the embodiment are described.

(Modification to the Indicator 7)

The indicator 7 may be modified such that it uses only sound as the presentation method thereof and calculates a difference between the distances between the two sensors 6 and the mark body 3 from outputs of the two sensors 6 and then performs presentation by high/low and/or strong/weak of sound based on the difference. Where the modified configuration is adopted, since the sound changes (for example, the sound volume decreases) upon insertion of the applicator 4 and the direction of the change of the sound reverses (for example, the sound volume increases) when the applicator 4 passes its optimum position, the user can discriminate the position upon the change as the optimum position. Thus, the user can move back the excessively inserted applicator 4 and position the applicator 4 at the optimum position.

(Warning Display)

At step S52 described above, the system 1 performs such warning display as seen in FIG. 9. According to the warning display, also the error from the optimum position of the applicator 4 stored at step S36 can be displayed. For example, where there is an error of +3 mm in the insertion direction of the applicator 4, that there is a displacement of +3 mm can be displayed together with a display of displacement as seen in FIG. 9. Here, the error is calculated based on the distance to the mark body 3 determined from the times required for back and forth travel of ultrasonic waves between the two sensors 6 and the mark body 3.

Details are described with reference to FIG. 8. If the position of the applicator 4 is displaced from the optimum position, then the distance Da from the sensor 6a to the mark body 3 and the distance Db from the sensor 6b to the mark body 3 become different from each other. The distances from the sensors 6a and 6b to the intersecting point I can be calculated based on the values of the distances Da and Db at this time, respectively. The error can be calculated by comparing the distance values then with the distance from the sensor 6a to the intersecting point I when the applicator 4 is at the optimum position.

Here, upon warning display, it is discriminated which one of the distances from the sensor 6a on the distal end side and the sensor 6b on the proximal end side is greater to discriminate whether the applicator 4 is displaced to the distal end side or the proximal end side, and a result of the discrimination is displayed. More particularly, when the distance between the mark body 3 and the sensor 6a on the distal end side is greater than the distance between the mark body 3 and the sensor 6b on the proximal end side, it is discriminated that the applicator 4 is displaced to the distal end side, and a display for urging the user to draw the applicator 4 to the proximal end side is displayed. On the contrary, when the distance between the mark body 3 and the sensor 6a on the distal end side is smaller, it is discriminated that the applicator 4 is displaced to the proximal end side, and a display for urging the user to push the applicator 4 to the distal end side is displayed.

(Modifications to the Sensors)

<Number of Sensors>

The embodiment described above involves two sensors 6. However, the number of sensors 6 may be greater than two or otherwise be one. The accuracy can be raised as the number of sensors 6 increases. Also where the number of sensors 6 is greater than two, the optimum position of the applicator 4 can be determined by calculating the distance to the mark body 3 similarly as in the case where the number of sensors 6 is two. Therefore, overlapping description of the determination of an optimum position of the applicator 4 is omitted herein to avoid redundancy.

A technique for discriminating an optimum position of the applicator 4 where the number of sensors 6 is one is described. The sensor 6 is attached to the applicator 4 at a position corresponding to the center of the energy emitter 5. In particular, the sensor 6 and the center of the energy emitter 5 are juxtaposed on a straight line in a radial direction of the applicator 4. Here, it is assumed that the mark body 3 is disposed at the center of the affected part by the user in accordance with the processes up to step S14 described hereinabove.

As described above, the sensor 6 oscillates an ultrasonic wave to the mark body 3 and measures the period of time before it receives the ultrasonic wave reflected from the mark body 3 to calculate the distance to the mark body 3. This is also possible where the number of sensors 6 is one, that is, only one sensor 6 is involved. However, different from the case wherein two sensors 6 are involved, it is impossible to discriminate an optimum position from the fact that the distances to the mark body 3 are equal to each other.

Here, the control apparatus 70 successively detects the distance to the mark body 3 using the single sensor 6 and stores the thus detected distance values into the storage section 71 so that they can be compared with each other. As the insertion of the applicator 4 proceeds, initially the distance to the mark body 3 detected exhibits a decrease, but after the mark body 3 is passed, the detected distance now exhibits an increase. Accordingly, the position of the applicator 4 at which the distance begins to increase is the optimum position of the applicator 4. Based on this, the control apparatus 70 can successively measure the distance between the mark body 3 and the sensor 6 and compare the measured distance values, and can discriminate the position at which the sensor 6 is positioned nearest to the mark body 3 as the optimum position of the applicator 4.

<Voltage Detection by the Sensor>

Also it is possible for each of the sensors 6 to detect the intensity of an ultrasonic wave upon reception of the ultrasonic wave as a voltage. In this instance, even if the back and forth travel time of the ultrasonic wave between the sensor 6 and the mark body 3 is not measured as described above, the optimum position of the applicator 4 can be discriminated. A capacity of the sensor 6 for detecting a voltage of an ultrasonic wave is described under the following particular conditions.

(1) A PZT (lead zirconate titanate) oscillator having a high gain at 15 MHz is used as the sensor 6.

(2) A metal chip (flat plate of stainless steel) having a diameter of 5 mm is used as the mark body 3.

(3) The mark body 3 of (2) is adhered to the glove 2 and water is infused into between the inside of the glove 2 and the hand.

(4) The glove 2 is disposed so that the mark body 3 may be positioned at a distance of 22 mm from the sensor 6. The position of the glove 2 is fixed. It is to be noted that the distance of 22 mm is an average distance from the rectum to the urethra among patients of the prostatic hypertrophy.

Figure 10:
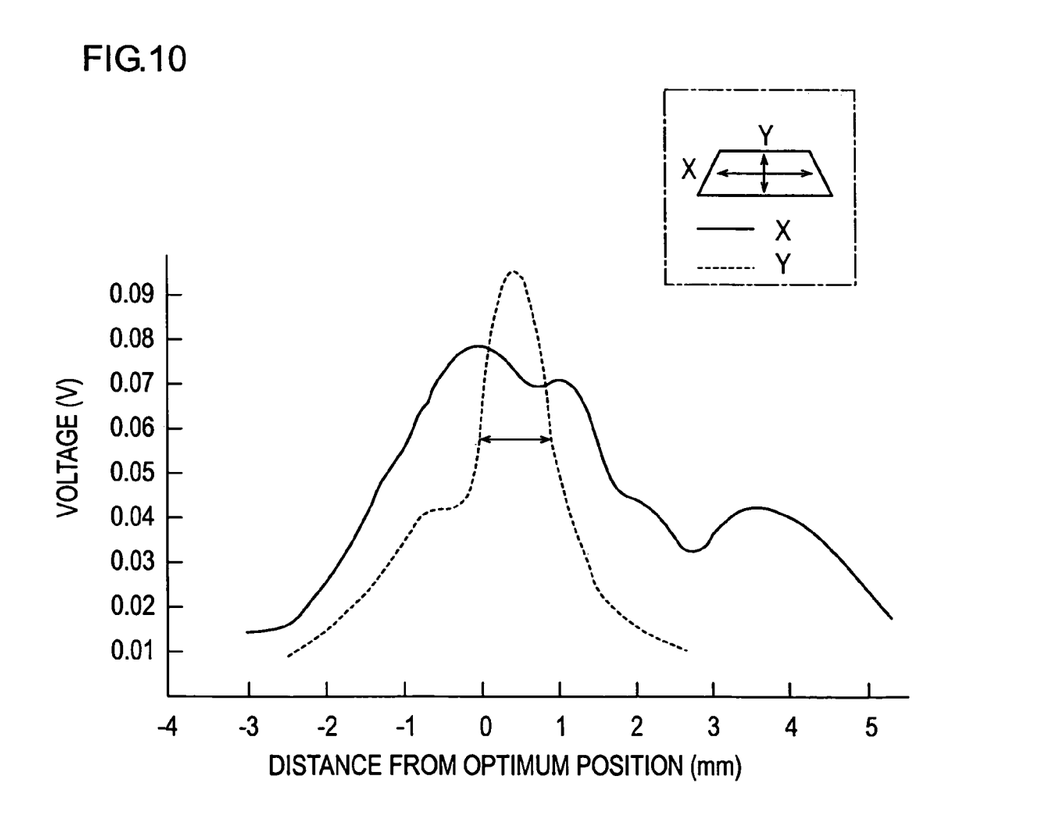
FIG. 10 is a diagram illustrating a relationship between the relative distance between a sensor and the mark body and the voltage detected by the sensor.

Under the conditions, the sensor 6 was moved parallelly with respect to the mark body 3. The parallel movement was performed in a certain one direction (X direction: for example, the direction of the longitudinal axis of the insertion portion 43) and a perpendicular direction (Y direction). At this time, a result illustrated in FIG. 10 was obtained. FIG. 10 is a view illustrating a relationship between the relative distance between the sensor 6 and the mark body 3 and the voltage detected by the sensor 6. The axis of abscissa indicates the relative distance between the sensor 6 and the mark body 3, and the axis of ordinate indicates the voltage. In FIG. 10, the relationship when the sensor 6 was moved in the X direction is indicated by a solid line, and the relationship when the sensor 6 was moved in the Y direction is indicated by a broken line.

As seen from FIG. 10, as the relative distance between the sensor 6 and the mark body 3 decreases, the voltage detected exhibits a sudden increase. Particularly where the sensor 6 is moved in the Y direction, the voltage variation is significant and can be discriminated on the order of 1 mm in the distance of movement. On the other hand, it is considered that the reason why such a significant voltage variation is not obtained where the sensor 6 is moved in the X direction depends upon the posture of the sensor 6 or unevenness of the wave front of the ultrasonic wave transmitted.

In this manner, also where the sensor 6 which can detect an ultrasonic wave as a voltage is used, it is considered based on the variation of the output voltage of the sensor 6 that the position at which the voltage value exhibits its peak value is the optimum position of the applicator 4.

Accordingly, the sensor 6 can be applied to the system 1 for the applicator 4.

<Magnetic Sensor>

A magnetic sensor can be used in place of the ultrasonic wave sensor 6. As the magnetic sensor, a magnetic sensor which can measure a magnetic field with a high degree of accuracy such as an MI sensor or an MR sensor is preferably used. Where a magnetic sensor is used, a magnetic material such as a magnet or an induction coil is used as the mark body 3. The magnetic sensor can measure the distance to the mark body 3 based on a magnetic field generated by the magnetic material or the induction coil.

<Form of the Sensor>

Figure 11:
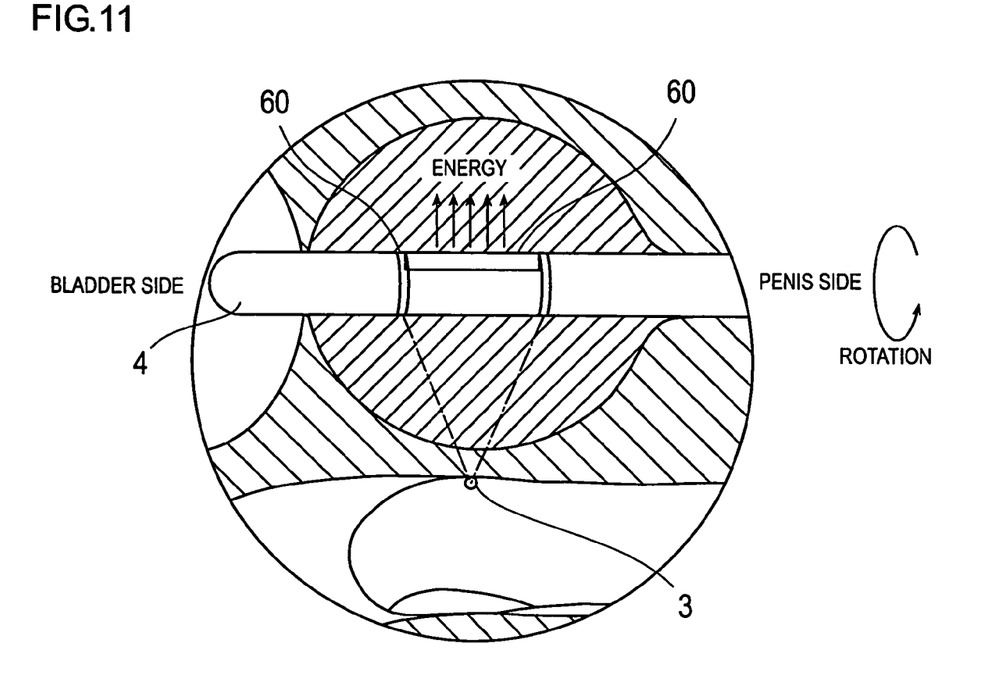
FIG. 11 is a view showing a sensor of a modified shape.

FIG. 11 is a view showing a modified form of the sensor 6.

In the embodiment described hereinabove, the sensors 6 are disposed at one point on a circumference of the applicator 4. However, the ultrasonic sensors can be provided along an outer periphery of the applicator 4 of a cylindrical shape as shown in FIG. 11. Where a PZT oscillator is used, a plurality of ultrasonic wave sensors 60 are disposed in an array on the applicator 4. The ultrasonic wave sensors 60 can be formed in an elongated shape using a piezoelectric polymer such as PVDF as a material therefor and disposed around the applicator 4.

Where the ultrasonic wave sensors are provided along the outer periphery of the applicator 4 in this manner, even if the applicator 4 is rotated around its axis for treatment of the affected part, ultrasonic waves reflected from the mark body 3 can be received by the ultrasonic wave sensors 60, and consequently, the optimum position of the applicator 4 can be discriminated. This is particularly effective when the prostate is treated from the urethra over the range of 360° around the urethra as in the treatment of the prostatic hypertrophy.

(Discrimination Time Before Interruption of Treatment)

The period of time, at step S53 of the embodiment described above, before interruption of the treatment is discriminated after a positional displacement occurs is set to 3 seconds. However, the period of time may be set to any period only if no damage to the living body occurs even if energy is supplied in response to a positional displacement.

(Energy Emitter)

The energy emitter 5 may supply energy not only in the form of a magnetic waveform but also in the form of an acoustic wave or electric current to the affected part. This makes it possible to treat the affected part using the energy in the form of an acoustic wave or electric current.

(Other Application)

In the embodiment described above, the positioning system 1 for the applicator 4 is used for the treatment of the prostatic hypertrophy. However, it can be applied not only to the treatment of the prostatic hypertrophy but also to the treatment of any other part. For example, in the treatment of the esophagi, it is possible to use the glove 2 to palpate the affected part extracorporeally from the throat, the breast or the belly to dispose the mark body 3 at the position of the affected part and then insert the applicator 4 from the mouth and present the optimum position of the applicator 4 to the user in such a manner as described hereinabove.

(Replacement of the Mark Body and the Sensors)

In the embodiment described above, the mark body 3 is provided on the glove 2 while the sensors 6 are provided on the applicator 4. However, it is otherwise possible to replace the mark body 3 and the sensor 6 with each other such that the sensors 6 are provided on the glove 2 and the mark body 3 is provided on the applicator 4. The arrangement in this instance is different from the embodiment described hereinabove in addition to the replacement of the positions at which the mark body 3 and the sensors 6 are provided only in that the control apparatus 70 and the display apparatus 8 are connected to the glove 2 side. Therefore, detailed description of the arrangement is omitted herein to avoid redundancy.

The user would use the glove 2 with the sensors 6 to palpate the affected part of the patient to dispose the sensors 6 in the proximity of the affected part. Consequently, the positioning system for the applicator 4 detects the mark body 3 provided on the applicator 4 by means of the sensors 6, discriminates the optimum position of the applicator 4 based on the detected distances and displays the optimum position on the display apparatus 8.

Accordingly, also with the present modified system, the user can position the applicator 4 readily at the affected part in accordance with the display of the display apparatus 8.

(Effects of the Invention)

Since the mark body is provided on the diagnosing implement, while a doctor or the like palpates the affected part of a patient using the diagnosing implement, it can dispose the mark body using the same as a mark representative of the position of the affected part. Since the distance to the mark body can be detected by means of the sensor, the optimum position of the applicator can be discriminated based on the detected distance. Since a result of the discrimination is presented by means of the presentation means, the user can position the applicator readily at the affected part in accordance with the presentation.

The mark body can be detected readily by means of the elastic wave sensor or the magnetic sensor.

Since the ultrasonic wave sensor oscillates an ultrasonic wave and besides receives the ultrasonic wave, the applicator is simplified in configuration and the diameter thereof can be reduced. Consequently, the burden on the patient can be reduced. Further, since the mark body has an acoustic impedance different from that of the living body, it can be detected with certainty by the ultrasonic wave sensor.

Also where the applicator is rotated to perform treatment of the affected part, the mark body can be detected by means of the ultrasonic wave sensor, and the optimum position of the applicator can be discriminated.

The single sensor can be used to successively measure the distance between the mark body and the sensor and compare the measured distance values, and when the sensor is positioned nearest to the mark body, the optimum position of the applicator can be discriminated readily.

Where two sensors are provided, when the distances between the sensors and the mark body coincide with each other, the position of the applicator then can be determined decisively as the optimum position of the applicator.

The optimum position of the applicator can be confirmed using at least one of the visual sense and the auditory sense.

When the position of the applicator is displaced from the optimum position, since a warning is presented by an image or by sound, the warning can be confirmed using at least one of the visual sense and the auditory sense.

Energy of any one of an acoustic wave, an electromagnetic wave and electric current can be supplied to the living body to treat the affected part.

Since the mark body can be sterilized, it can be inserted into the living body without the possibility of an infectious disease.

The prostatic hypertrophy can be treated.

Since the mark body is formed in a shape and a size which have no influence on the palpation, the user can perform palpation and so forth without suffering from any degradation of the feeling of the fingertip.

Since the sensor is provided on the diagnosing implement, while a doctor or the like palpates the affected part of a patient using the diagnosing implement, it can dispose the sensor at the position of the affected part. Since the sensor can detect the distance to the mark body provided on the applicator, the optimum position of the applicator can be discriminated based on the detected distance. Since a result of the discrimination is presented by means of the presentation means, the user can position the applicator readily at the affected part in accordance with the presentation.

The entire disclosure of Japanese Patent Application No. 2003-087932 filed on Mar. 27, 2003 including specification, claims, drawings, and summary are incorporated herein by reference in its entirety.

What is claimed is:

1. A positioning system for an applicator, comprising:
   a diagnosing implement to diagnose a living body including an affected part;
   a mark body provided on said diagnosing implement;
   an applicator;
   an energy emitter provided in said applicator and emitting energy to the living body;
   at least one sensor provided on said applicator for outputting a signal corresponding to a distance between the sensor and said mark body; and
   an indicator which indicates a preferable position of said applicator based on the output of said sensor while said mark body is disposed in the proximity of the affected part through a diagnosis performed using said diagnosing implement.

2. A positioning system for an applicator according to claim 1, wherein said sensor is an elastic wave sensor or a magnetic sensor, and said positioning system comprises a single or a plurality of such sensors.

3. A positioning system for an applicator according to claim 2, wherein said elastic wave sensor is an ultrasonic sensor and serves also as an ultrasonic wave oscillator, and said mark body is an ultrasonic wave reflecting body having an acoustic impedance different from that of the living body.

4. A positioning system for an applicator according to claim 2, wherein said applicator is formed in a cylindrical shape, and said elastic wave sensor is provided on an outer peripheral face of the cylinder of said applicator such that, even if said applicator rotates around an axis thereof, said elastic wave sensor can receive an ultrasonic wave from a plurality of directions.

5. A positioning system for an applicator according to claim 1, wherein said indicator includes a processor which discriminates the optimum position of said applicator based on the output of said sensor.

6. A positioning system for an applicator according to claim 5, wherein said positioning system comprises a single sensor, and said processor discriminates a position at which said sensor is positioned nearest to said mark body as the optimum position of said applicator.

7. A positioning system for an applicator according to claim 5, wherein said processor stores the distance between said sensor and said mark body when it is discriminated that said applicator is at the optimum position and discriminates a positional displacement when an error of the distance to said mark body detected by said sensor during the diagnosis from the stored distance becomes equal to or higher than a predetermined value, and said indicator indicates, when said processor discriminates a positional displacement, a warning of the positional displacement by at least one of an image and sound.

8. A positioning system for an applicator according to claim 1, wherein said positioning system comprises two sensors provided on a straight line parallel to an insertion direction of said applicator, and said indicator indicates a position at which the distances between said sensors and said mark body are equal to each other as the optimum position of said applicator.

9. A positioning system for an applicator according to claim 1, wherein said indicator indicates the optimum position of said applicator by at least one of an image and sound.

10. A positioning system for an applicator according to claim 1, wherein said energy emitter emits energy of an electromagnetic wave, an acoustic wave or electric current to the living body.

11. A positioning system for an applicator according to claim 1, wherein said mark body allows sterilization to be incorporated into and introduced together with said diagnosing implement into the living body.

12. A positioning system for an applicator according to claim 1, wherein said applicator has an insertion portion, which is formed to insert into the urethra and treats the prostatic hypertrophy and said energy emitter is provided in said insertion portion, and said diagnosing implement is a glove for being used to palpate the affected part from the rectum while said mark body is disposed in the proximity of the affected part through the palpation.

13. A positioning system for an applicator according to claim 12, wherein said mark body is formed in a shape and a size which do not have an influence on the palpation performed using said glove.

14. A positioning system for an applicator, comprising:
   an applicator;
   an energy emitter provided in said applicator and emitting energy to a living body;
   a mark body provided on said applicator;
   a diagnosing implement to diagnose of a living body including an affected part;
   a sensor provided on said diagnosing implement and capable of detecting a distance between the sensor and said mark body; and
   an indicator which indicates a preferable position of said applicator based on an output of said sensor while said sensor is disposed in the proximity of the affected part through the diagnosis performed using said diagnosing implement.

15. A positioning method for an applicator, comprising the steps of:

diagnosing a living body including an affected part with a diagnosing implement which has a mark body, specifying the position of the affected part and disposing the mark body in the proximity of the affected part;

inserting an applicator having a sensor capable of detecting the distance between the sensor and said mark body into the living body; and positioning said applicator in response to information indicated corresponding to an output of said sensor, wherein said mark body is sterilized and incorporated into and introduced together with said diagnosing implement into the living body.

16. A positioning method for an applicator according to claim 15, wherein the indication of the information is a notification which depends upon high/low and/or strong/weak of sound corresponding to the distance between said mark body and said sensor.

17. A positioning method for an applicator according to claim 15, wherein the information is information discriminated by a processor based on the output of said sensor.

18. A positioning method for an applicator according to claim 17, wherein said processor stores the distance between said sensor and said mark body when it is discriminated that said applicator is at the optimum position and discriminates a positional displacement when an error of the distance to said mark body detected by said sensor from the stored distance becomes equal to or higher than a predetermined value, and presents a warning of the positional displacement by at least one of an image and sound.

19. A positioning method for an applicator according to claim 15, wherein said diagnosing implement is a glove for being used to palpate the affected part from the rectum, and said mark body is provided at a fingertip of said glove and disposed in the proximity of the affected part through the palpation.

20. A positioning method for an applicator according to claim 15, wherein said applicator is inserted from the urethra and positioned at the prostate.

21. A positioning method for an applicator, comprising the steps of:

diagnosing a living body including an affected part with a diagnosing implement which has a sensor specifying the position of the affected part and disposing the sensor in the proximity of the affected part;

inserting an applicator having a mark body into a living body;

detecting the distance between said sensor and the mark body; and positioning said applicator in response to information detected by said sensor.

* * * * *